United States Patent [19]

Langbein et al.

[11] 4,087,531
[45] May 2, 1978

[54] N-(3-(P-FLUORO-BENZOYL)-N-PROPYL)-4-(IMIDAZOLIDIN-2-ONE-1-YL)-PIPERIDINES AND SALTS THEREOF

[75] Inventors: Adolf Langbein, Ingelheim am Rhein; Gerhard Walther, Bingen, am Rhein; Peter Danneberg, Ockenheim; Franz Josef Kuhn, Bingen, am Rhein, all of Germany

[73] Assignee: Boehringer Ingelheim GmbH, Ingelheim am Rhein, Germany

[21] Appl. No.: 730,123

[22] Filed: Oct. 6, 1976

Related U.S. Application Data

[63] Continuation-in-part of Ser. No. 575,941, May 9, 1975, abandoned.

[30] Foreign Application Priority Data

May 16, 1974 Germany .......................... 2423896

[51] Int. Cl.² ................. C07D 401/04; A61K 31/445
[52] U.S. Cl. ................................... 424/267; 260/293.7
[58] Field of Search ..................... 260/293.7; 99/407; 424/267

[56] References Cited

U.S. PATENT DOCUMENTS

| 3,459,757 | 8/1969 | Wright et al. | 260/239.7 |
| 3,922,266 | 11/1977 | Katsube et al. | 260/293.7 |
| 3,956,339 | 5/1976 | Wilhelm et al. | 260/293.7 |

Primary Examiner—Henry R. Jiles
Assistant Examiner—Robert T. Bond
Attorney, Agent, or Firm—Hammond & Littell

[57] ABSTRACT

Compounds of the formula

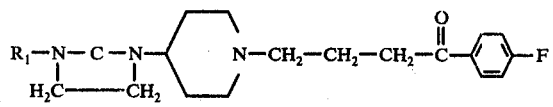

wherein $R_1$ is hydrogen, acetyl, alkyl of 1 to 3 carbon atoms or phenyl, and non-toxic, pharmacologically acceptable acid addition salts thereof; the compounds as well as their salts are useful as CNS-depressants, sedatives and tranquilizers.

6 Claims, No Drawings

N-(3-(P-FLUORO-BENZOYL)-N-PROPYL)-4-(IMIDAZOLIDIN-2-ONE-1-YL)-PIPERIDINES AND SALTS THEREOF

This is a continuation-in-part of copending application Ser. No. 575,941 filed May 9, 1975, now abandoned.

The present invention relates to novel N-[3'-p-fluorobenzoyl) -n-propyl]-4-(imidazolidin-2-one-1-yl)-piperidines and acid addition salts thereof, as well as to methods of preparing these compounds.

More particularly, the present invention relates to a novel class of N-(p-fluorobenzoyl-n-propyl)-4-(imidazolidin-2-one-1-yl)-piperidines represented by the formula

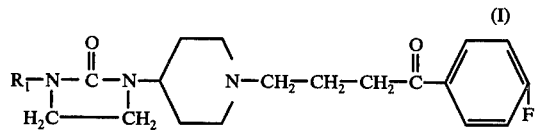

wherein $R_1$ is hydrogen, acetyl, alkyl of 1 to 3 carbon atoms or phenyl, and non-toxic, pharmacologically acceptable acid addition salts thereof.

The compounds embraced by formula I above may be prepared by the following methods.

METHOD A

By alkylating a 4-(imidazolidin-2-one-1-yl)-piperidine of the formula

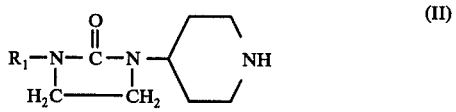

wherein $R_1$ has the same meanings as in formula I, with a p-fluoro-butyrophenone of the formula

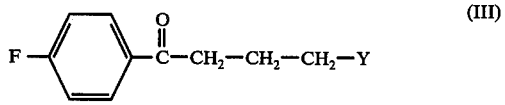

wherein Y is halogen, especially chlorine, bromine or iodine, phenylsulfonyl, toluenesulfonyl, alkylsulfonyl or the like.

The alkylation is carried out in conventional manner, preferably in the presence of an acid-binding agent, with the starting compound of the formula III being provided in the stoichiometric amount or in excess thereover. Examples of suitable acid-binding agents are triethylamine, N,N-dicyclohexyl-ethylamine, sodium carbonate, potassium carbonate, calcium oxide or, preferably, sodium bicarbonate.

Although the performance of the reaction in a solvent medium is not absolutely essential, it is advantageous to add an inert solvent to the reaction mixture. Examples of suitable inert solvents are lower alkanols, chloroform, toluene, nitromethane, tetrahydrofuran or, preferably, dimethylformamide; mixtures of any two or more of these solvents may also be used.

The optimum alkylation reaction temperature may vary within wide limits, depending upon the reactivity of the reactants, but generally lies between 50° and 150° C. However, the reflux temperature of the reaction mixture is preferred.

The addition of from catalytic to molar amounts of potassium iodide or sodium iodide to the reaction mixture is of advantage in some instances.

METHOD B

For the preparation of a compound of the formula I wherein $R_1$ is acetyl, by acetylating a compound of the formula I wherein $R_1$ is hydrogen with acetyl chloride or acetic acid anhydride.

The compounds embraced by formula I are organic bases and therefore form acid addition salts with inorganic or organic acids. Examples of non-toxic, pharmacologically acceptable acid addition salts are those formed with a hydrohalic acid, nitric acid, sulfuric acid, orthophosphoric acid, oxalic acid, citric acid, tartaric acid, fumaric acid, maleic acid, propionic acid, butyric acid, acetic acid, methanesulfonic acid, toluenesulfonic acid, sulfonilic acid, succinic acid, 8-chlorotheophylline or the like.

The starting compounds of the formulas II and III are known compounds or may be prepared in analogy to known methods. Compounds of the formula II, for instance, may be prepared by the method described in German Offenlegungsschrift No. 2,341,229.

The following examples illustrate the present invention and will enable others skilled in the art to understand it more completely. It should be understood, however, that the invention is not limited solely to the particular examples given below.

EXAMPLE 1

N-[3'-(p-Fluoro-benzoyl)-n-propyl]-4-(imidazolidin-2-one-1-yl)-piperidine and its hydrochloride by method A A mixture consisting of 1.69 gm (10 millimols) of 4-(imidazolidin-2-one-1-yl)-piperidine, 2.2 gm (11 millimols) of p-fluoro-ω-chloro-butyrophenone, 1.26 gm (15 millimols) of sodium bicarbonate, 1.66 gm (10 millimols) of potassium iodide and 25 ml of dimethylformamide was stirred at a temperature of 100° C for 2 hours, and the suspension obtained thereby was evaporated in a rotary evaporator at 70° C as far as possible. The residue was taken up in a mixture of 250 ml of methylene chloride and 100 ml of water, and the organic phase was subsequently extracted 5 times with 125 ml each of water. After drying over sodium sulfate, the organic phase was filtered and the filtrate was evaporated. The residual oil was dissolved in 10 ml of ethanol, the solution was admixed with 2 ml of 5 N ethanolic hydrochloric acid, and subsequently 60 ml of ether were carefully added, whereupon 1.9 gm (51.5% of theory) of the crystalline hydrochloride of the formula

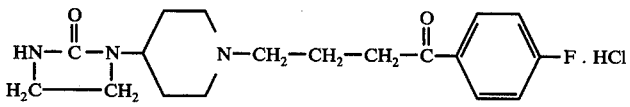

crystallized out.

EXAMPLE 2

N-[3'-(p-Fluoro-benzoyl)-n-propyl]-4-[3-acetyl-imidazolidin-2-one-1-yl]-piperidine and its hydrochloride by method B 4.71 ml (50 millimols) of acetic acid anhydride were added to a solution of 3.3 gm (10 millimols) of N-[3'-(p-fluoro-benzoyl)-n-propyl]-4-(imidazolidin-2-one-1-yl)-piperidine (see Example 1) in 25 ml of benzene, and the mixture was refluxed for five hours. Thereafter, the reaction solution was evaporated in a rotary evaporator, the residue was made alkaline with ammonia, and the alkaline mixture was extracted three times with 50 ml each of methylene chloride. The combined organic extracts were dried and evaporated, the residue was dissolved in ethanol, the resulting solution was admixed with the calculated amount of ethanolic hydrochloric acid, and then ether was added, whereupon 3 gm (73% of theory) of the hydrochloride, m.p. 257°–258° C, of the formula

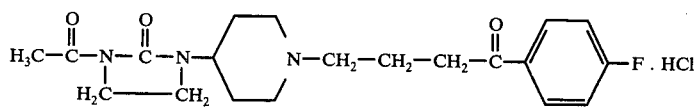

crystallized out.

The compounds of the present invention, that is, those embraced by formula I above and their non-toxic, pharmacologically acceptable acid addition salts, have useful pharmacodynamic properties. More particularly, the compounds of this invention exhibit the characteristic desirable activity picture of neuroleptics in warm-blooded animals, such as mice and rats, and are therefore useful as CNS-depressants, sedatives and tranquilizers.

However, whereas it can be shown in animal tests that known neuroleptics exhibit strong antagonistic activities against epinephrine, amphetamine and apomorphine, the compounds of the present invention exhibit only strong antagonistic activities against epinephrine, but no amphetamine or apomorphine-antagonistic activities.

The strong apomorphine-antagonistic activity of known neuroleptics is the cause of more or less pronounced extrapyramidal side-effects, especially in the case of administration thereof over prolonged periods of time and high dosages. The absence of apomorphine and amphetamine-antagonistic activities of the compounds of the present invention leads to the conclusion that the above-mentioned undesirable side-effects upon the dopaminergic extrapyramidal system can be at least substantially reduced, if not entirely suppressed.

In addition, the toxicities of the compounds of the present invention are significantly lower than those of known neuroleptics of related structure; for example, whereas the $LD_{50}$ of haloperidol is about 170 mgm/kg p.o., the $LD_{50}$ of the compounds of this invention is generally from 1000 to 2000 mgm/kg p.o. and in some cases even considerably higher.

For pharmaceutical purposes the compounds according to the present invention are administered to warm-blooded animals perorally, or parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0083 to 0.167 mgm/kg body weight, preferably 0.016 to 0.084 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 3

COATED PILLS

The pill core composition is compounded from the following ingredients:

| | |
|---|---|
| N-[3'-(p-Fluoro-benzoyl)-n-propyl]-4-(imidazolidin-2-one-1-yl)-piperidine hydrochloride | 2.0 parts |
| Lactose | 28.5 parts |
| Corn starch | 17.0 parts |
| Gelatin | 2.0 parts |
| Magnesium stearate | 0.5 parts |
| Total | 50.0 parts |

Preparation:

The piperidine compound is intimately admixed with the lactose and the corn starch, the mixture is moistened with an aqueous 10% solution of the gelatin, and the moist mass is granulated by forcing it through a 1 mm-mesh screen. The granulate thus obtained is dried at 40° C, again passed through the screen and admixed with the magnesium stearate, and the composition is compressed into 50 mgm-pill cores which are subsequently coated with a thin shell consisting essentially of a mixture of sugar, titanium dioxide, talcum and gum arabic, and finally polished with beeswax. Each coated pill contains 2 mgm of the piperidine compound and is an oral dosage unit composition with effective neuroleptic action.

EXAMPLE 4

TABLETS

The tablet composition is compounded from the following ingredients:

| | |
|---|---|
| N-[3'-(p-Fluoro-benzoyl)-n-propyl]-4-(3-acetyl-imidazolidin-2-one-1-yl)-piperidine hydrochloride | 2.0 parts |
| Lactose | 55.0 parts |
| Corn starch | 38.0 parts |
| Soluble starch | 4.0 parts |
| Magnesium stearate | 1.0 parts |
| Total | 100.0 parts |

Preparation:

The piperidine compound and the magnesium stearate are intimately admixed with each other, the mixture is moistened with an aqueous solution of the soluble starch and granulated as described in the preceding example, the granulate is dried and then intimately admixed with the lactose and the corn starch, and the composition is compressed into 100 mgm tablets in a conventional tablet making machine. Each tablet contains 2 mgm of the piperidine compound and is an oral dosage unit composition with effective neuroleptic action.

EXAMPLE 5

SUPPOSITORIES

The suppository composition is compounded from the following ingredients:

| | | |
|---|---|---|
| N-[3'-(p-Fluoro-benzoyl)-n-propyl]-4-(imidazolidin-2-one-1-yl)-piperidine hydrochloride | | 1.0 parts |
| Suppository base (e.g. cocoa butter) | | 1699.0 parts |
| | Total | 1700.0 parts |

Preparation:

The suppository base is melted and cooled to 40° C, the finely powdered piperidine compound is blended into the suppository base with the aid of an immersion homogenizer, and 1700 mgm portions of the compositions are poured into cooled suppository molds and allowed to harden therein. Each suppository contains 1 mgm of the piperidine compound and is a rectal dosage unit composition with effective neuroleptic action.

EXAMPLE 6

HYPODERMIC SOLUTION

The solution is compounded from the following ingredients:

| | | |
|---|---|---|
| N-(3'-(p-Fluoro-benzoyl)-n-propyl]-4-(3-acetyl-imidazolidin-2-one-1-yl)-piperidine hydrochloride | | 2.0 parts |
| Sodium chloride | | 18.0 parts |
| Distilled water | q.s.ad | 2000.0 parts by water |

Preparation:

The piperidine compound and the sodium chloride are dissolved in the distilled water, the solution is filtered until free from suspended particles, and the filtrate is filled into 2 cc-ampules under aseptic conditions, which are subsequently sterilized and sealed. Each ampule contains 2 mgm of the piperidine compound, and its contents are an injectable dosage unit composition with effective neuroleptic action.

Analogous results are obtained when any one of the other piperidine compounds embraced by formula I or a non-toxic, pharmacologically acceptable acid addition salt thereof is substituted for the particular piperidine compound in Examples 3 through 6. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

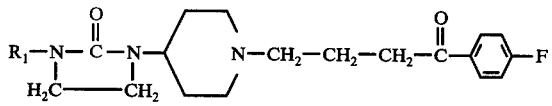

wherein $R_1$ is hydrogen, acetyl, alkyl of 1 to 3 carbon atoms or phenyl, or a non-toxic, pharmacologically acceptable acid addition salt thereof.

2. A compound of claim 1, where $R_1$ is hydrogen or acetyl.

3. A compound of claim 1, which is N-[3'-(p-fluoro-benzoyl)-n-propyl]-4-(3-acetyl-imidazolidin-2-one-1-yl)-piperidine or a non-toxic, pharmacologically acceptable acid addition salt thereof.

4. A compound of claim 1, which is N-[3'-(p-fluoro-benzoyl)-n-propyl]-4-(imidazolidin-2-one-1-yl)-piperidine or a non-toxic, pharmacologically acceptable acid addition salt thereof.

5. A neuroleptic pharmaceutical dosage unit composition consisting essentially of an inert pharmaceutical carrier and an effective CNS-depressing, sedative or tranquilizing amount of a compound of claim 1.

6. The method of depressing the central nervous system of a warm-blooded animal in need of such treatment, which comprises perorally, parenterally or rectally administering to said animal an effective CNS-depressing, sedative or tranquilizing amount of a compound of claim 1.

* * * * *